United States Patent
Ma et al.

(10) Patent No.: US 11,940,375 B2
(45) Date of Patent: Mar. 26, 2024

(54) FIBER-OPTIC PHOTOACOUSTIC SENSING PROBE CAPABLE OF RESISTING INTERFERENCE FROM AMBIENT NOISE, AND SENSING SYSTEM

(71) Applicants: STATE GRID ANHUI ELECTRIC POWER RESEARCH INSTITUTE, Anhui (CN); Dalian University of Technology, Liaoning (CN)

(72) Inventors: Fengxiang Ma, Anhui (CN); Ke Chen, Liaoning (CN); Yue Zhao, Anhui (CN); Feng Zhu, Anhui (CN); Min Guo, Liaoning (CN); Yu Tian, Anhui (CN); Xiaofang Yuan, Anhui (CN); Yabin Ma, Anhui (CN); Chen Hang, Anhui (CN)

(73) Assignees: STATE GRID ANHUI ELECTRIC POWER RESEARCH INSTITUTE, Hefei (CN); Dalian University of Technology, Dalian (CN)

( * ) Notice: Subject to any disclaimer, the term of this patent is extended or adjusted under 35 U.S.C. 154(b) by 372 days.

(21) Appl. No.: 17/535,978

(22) Filed: Nov. 26, 2021

(65) Prior Publication Data
US 2022/0178816 A1 Jun. 9, 2022

Related U.S. Application Data

(63) Continuation of application No. PCT/CN2021/121019, filed on Sep. 27, 2021.

(30) Foreign Application Priority Data
Dec. 8, 2020 (CN) .......................... 202011424469.X

(51) Int. Cl.
*G01N 33/00* (2006.01)
*G01N 21/17* (2006.01)

(52) U.S. Cl.
CPC ..... *G01N 21/1702* (2013.01); *G01N 33/0027* (2013.01); *G01N 2021/1704* (2013.01);
(Continued)

(58) Field of Classification Search
CPC ........... G01N 21/1702; G01N 33/0027; G01N 2021/1704; G01N 2201/06113; G01N 2201/08; G01N 21/8507
See application file for complete search history.

(56) References Cited

U.S. PATENT DOCUMENTS 11,300,499 B2 * 4/2022 Gong ................. G01N 21/1702
2021/0404949 A1 * 12/2021 Gong ................. G01N 21/1702

OTHER PUBLICATIONS

Sheng Zhou et al., Demonstration of a highly sensitive photoacoustic spectrometer based on a miniaturized all-optical detecting sensor, Optics Express, Jul. 24, 2017, pp. 17541-17548, vol. 25, No. 15.
(Continued)

*Primary Examiner* — Freddie Kirkland, III

(57) ABSTRACT

The present disclosure relates to the technical field of fiber-optic gas sensing and laser photoacoustic spectroscopy, and reliability of a gas detection system is improved by actively selecting a working frequency of low noise interference combined with an optical fiber photoacoustic sensing probe capable of isolating high-frequency noise. A gas enters a photoacoustic microcavity through gaps on a sound-sensitive diaphragm after diffusing into a miniature air chamber through a plurality of micropores. Photoacoustic excitation light is incident into the photoacoustic microcavity through a fiber-optic collimator and then excited to generate a photoacoustic pressure wave to cause the sound-sensitive diaphragm to vibrate periodically. An end face of a single-mode optical fiber and the sound-sensitive diaphragm constitutes a fiber-optic Fabry-Perot interferometer. The interferometer measures a deflection of the diaphragm and inverts a concentration of the to-be-measured gas.

18 Claims, 6 Drawing Sheets

(52) U.S. Cl.
CPC .............. *G01N 2201/06113* (2013.01); *G01N 2201/08* (2013.01)

(56) References Cited

OTHER PUBLICATIONS

Ke Chen et al., Fiber-optic Photoacoustic sensor for remote monitoring of gas micro-leakage, Optics Express, Feb. 18, 2019, pp. 4648-4659, vol. 27, No. 4.

\* cited by examiner

FIBER-OPTIC PHOTOACOUSTIC SENSING PROBE CAPABLE OF RESISTING INTERFERENCE FROM AMBIENT NOISE, AND SENSING SYSTEM

CROSS REFERENCE TO RELATED APPLICATIONS

The present application is a Continuation Application of PCT Application No. PCT/CN2021/121019 filed on Sep. 27, 2021, which claims the benefit of Chinese Patent Application No. 202011424469.X filed on Dec. 8, 2020. All the above are hereby incorporated by reference. the contents of which are incorporated herein by reference in their entirety.

TECHNICAL FIELD

The present disclosure belongs to the technical field of fiber-optic gas sensing and laser photoacoustic spectroscopy, and relates to a fiber-optic photoacoustic sensing probe capable of resisting interference from ambient noise, and a sensing system.

BACKGROUND

The trace gas detection technology has played an important role in fault characteristic gas analysis of electrical equipment, gas monitoring in environmental pollution, colliery safety monitoring, and other applications. At present, trace gas detection methods mainly include gas chromatography, electrochemical sensing, semiconductor gas-sensitive sensing, infrared absorption spectroscopy, photoacoustic spectroscopy, fiber-optic sensing, and the like. A fiber-optic gas sensing technology is essentially safe and supports remote measurement. It has incomparable advantages in gas monitoring in flammable and explosive environments such as petrochemical plants and collieries.

In principle, fiber-optic gas sensors mainly include a gas-sensitive sensor and a spectrum absorptive sensor. The gas-sensitive sensor uses a gas-sensitive material to modify fiber gratings, and changes a characteristic spectrum after a gas concentration changes. However, the gas-sensitive sensor has some disadvantages such as large cross interference, a slow response speed, and poor repeatability. An infrared spectral regime is a characteristic absorption spectrum band of most polar small and medium-sized gas molecules. Therefore, a to-be-measured gas can be measured remotely by combining an absorption spectrum technology and a fiber-optic sensing technology. The absorption spectroscopy mainly includes tunable diode laser absorption spectroscopy (TDLAS) and laser photoacoustic spectroscopy. Measurement sensitivity of the TDLAS is in direct proportion to an absorption optical path, a large gas absorption cell is usually required, and a detection limit of a fiber-optic gas sensor based on the TDLAS can only reach dozens of parts per million (ppm). However, detection sensitivity of the laser photoacoustic spectroscopy based on a one-way absorption photoacoustic cell has little to do with a length of the absorption optical path. A volume of the absorption photoacoustic cell can be accurate to milliliters, and a detection limit is easy to reach ppm.

In the prior art, a miniature fiber-optic photoacoustic gas sensor is disclosed by Zhou S, Slaman M, and Iannuzzi D, in the document Demonstration of a highly sensitive photoacoustic spectrometer based on a miniaturized all-optical detecting sensor[J]. Optics express, 2017, 25(15): 17541-17548; and by Chen K, Guo M, Liu S, et al. in the document Fiber-optic photoacoustic sensor for remote monitoring of gas micro-leakage[J]. Optics express, 2019, 27(4): 4648-4659. Both photoacoustic excitation light and photoacoustic detection light are transmitted by using an optical fiber, and a detection limit of acetylene gas can reach parts per billion (ppb).

However, as described in the above documents, the designed sensor uses a cantilever beam to detect a photoacoustic signal, and the cantilever beam can also respond to an acoustic wave signal in an environment, resulting in a concentration measurement error caused by interference from ambient noise. As a result, the fiber-optic photoacoustic gas sensor cannot be widely applied on site. Therefore, designing a high-sensitivity fiber-optic photoacoustic gas sensor immune to ambient noise has important application value.

SUMMARY

The present disclosure is intended to provide a fiber-optic photoacoustic gas sensing system and method that are capable of resisting interference from ambient noise, to avoid increasing a gas concentration measurement error because an existing fiber-optic photoacoustic gas sensor is easily prone to interference from ambient noise, and expand more space to apply a fiber-optic photoacoustic gas sensing technology to perform gas detection in a harsh environment.

The present disclosure resolves the technical problems by using following technical solutions:

A fiber-optic photoacoustic sensing probe (5) capable of resisting interference from ambient noise includes: a fiber-optic collimator (9), a single-mode optical fiber (10), a photoacoustic microcavity (11), a miniature air chamber (12), a diffusion micropore (13), a sound-sensitive diaphragm (14), and a sound-insulated housing (15), where the miniature air chamber (12) is provided inside the sound-insulated housing (15), the miniature air chamber (12) is cylindrical, and a plurality of diffusion micropores (13) communicating with the outside are provided along a diameter direction of the miniature air chamber (12); the sound-sensitive diaphragm (14) is installed inside the miniature air chamber (12), and includes a plurality of gaps (141) that constitute a cross-shaped beam structure at a central position of the sound-sensitive diaphragm (14); the photoacoustic microcavity (11) is deployed inside the sound-insulated housing (15) along a direction perpendicular to the miniature air chamber (12), one end of the photoacoustic microcavity (11) is connected to the outside, and the other end of the photoacoustic microcavity (11) is connected to the miniature air chamber (12); the fiber-optic collimator (9) is sealed and installed on the end, connected to the outside, of the photoacoustic microcavity (11); the single-mode optical fiber (10) is connected to the miniature air chamber (12) along a horizontal center line of the sound-insulated housing (15); and a center of the sound-sensitive diaphragm (14) and an end face of the single-mode optical fiber (10) constitute a fiber-optic Fabry-Perot interferometer.

The fiber-optic photoacoustic sensing probe (5) is provided with the sound-insulated housing (15) with the plurality of diffusion micropores (13), which not only retains a characteristic of diffusive gas measurement of a sensor, but also makes the fiber-optic photoacoustic sensing probe (5) capable of isolating high-frequency noise.

As a further improvement of the technical solutions of the present disclosure, a working process of the fiber-optic photoacoustic sensing probe (5) capable of resisting interference from ambient noise is as follows: a gas enters the photoacoustic microcavity (11) through the gaps (141) on the sound-sensitive diaphragm (14) after diffusing into the miniature air chamber (12) through the plurality of diffusion micropores (13); photoacoustic excitation light is incident into the photoacoustic microcavity (11) through the fiber-optic collimator (9), and then excited to generate a photoacoustic pressure wave to cause the sound-sensitive diaphragm (14) to vibrate periodically; and a deflection of the diaphragm is measured by using the fiber-optic Fabry-Perot interferometer, and a concentration of the to-be-measured gas is inverted.

A sensing system using the fiber-optic photoacoustic sensing probe (5) capable of resisting interference from ambient noise includes: a signal collection and processing circuit (1), a laser light source drive circuit (2), a photoacoustic excitation light source (3), a double-core optical fiber (4), a fiber-optic photoacoustic sensing probe (5), a detection light source (6), a fiber-optic circulator (7), and a photodetector (8), where an input terminal of the photodetector (8) is connected to port 3# of the fiber-optic circulator (7), and an output terminal of the photodetector (8), the signal collection and processing circuit (1), the laser light source drive circuit (2), and the photoacoustic excitation light source (3) are connected in series and then connected to the fiber-optic photoacoustic sensing probe (5) by using one optical fiber of the double-core optical fiber (4); the detection light source (6) is connected to port 1# of the fiber-optic circulator (7), and port 2# of the fiber-optic circulator (7) is connected to the fiber-optic photoacoustic sensing probe (5) by using the other optical fiber of the double-core optical fiber (4); and the signal collection and processing circuit (1) adopts a digital lock-in amplifier based on a field programmable gate array (FPGA).

The technical solutions of the present disclosure combine a method for actively selecting a working frequency and a narrowband detection technology of a lock-in amplifier. This greatly reduces an error caused by the ambient noise when a fiber-optic photoacoustic sensor measures a gas concentration, greatly improves reliability and stability of the system without increasing a cost of the fiber-optic photoacoustic sensing system, retains advantages of the system, for example, essential safety and support for remote measurement, and provides a highly competitive technical solution for highly sensitive and reliable fiber-optic gas sensing.

As a further improvement of the technical solutions of the present disclosure, a working process of the sensing system includes the following steps:
  step 1: turning off the photoacoustic excitation light source (3), where the detection light is reflected on a surface of the fiber-optic Fabry-Perot interferometer after entering the fiber-optic photoacoustic sensing probe (5), to output an interference signal;
  step 2: performing demodulation and spectrum analysis on the output interference signal to obtain influence of ambient noise, and then determining a low-interference frequency as a working frequency;
  step 3: driving the photoacoustic excitation light source (3) after determining a modulation frequency, where the excitation light is incident into the fiber-optic photoacoustic sensing probe (5) to cause a photoacoustic effect and generate a photoacoustic signal;
  step 4: restoring the photoacoustic signal by using an interference-intensity demodulation method, and performing spectrum analysis on the signal; and
  step 5: calculating a concentration of a to-be-measured gas based on an amplitude of the photoacoustic signal.

As a further improvement of the technical solutions of the present disclosure, a method for determining the low-interference frequency as the working frequency in step 2 is as follows: the detection light emitted by the detection light source (6) is incident into the fiber-optic photoacoustic sensing probe (5) after passing through the fiber-optic circulator (7), and returned Fabry-Perot interference signal light is received by the photodetector (8) after passing through the fiber-optic circulator (7); the signal collection and processing circuit (1) collects a photoelectric signal converted by the photodetector (8), restores an acoustic wave signal by using the interference-intensity demodulation method, and performs spectrum analysis on the detected ambient noise through fast Fourier transform; and the low-interference frequency in the ambient noise is selected, within a high frequency range and based on a frequency response of the fiber-optic photoacoustic sensing probe (5) to an external acoustic wave and a spectrum analysis result, as the working frequency of photoacoustic measurement.

As a further improvement of the technical solutions of the present disclosure, the modulation frequency in step 3 is set to half of the working frequency.

As a further improvement of the technical solutions of the present disclosure, the restoring the photoacoustic signal by using an interference-intensity demodulation method specifically includes: setting a central wavelength of the detection light source (6) to lock a working point at a position with a maximum absolute value of a slope of an interference curve of the fiber-optic Fabry-Perot interferometer used for photoacoustic detection (FIG. 6) in the fiber-optic photoacoustic sensing probe (5), so that acoustic wave detection has the highest sensitivity and a largest linear response range.

As a further improvement of the technical solutions of the present disclosure, the photoacoustic excitation light source (3) is a near-infrared wavelength-tunable narrow-linewidth laser light source that can be coupled to the single-mode optical fiber.

As a further improvement of the technical solutions of the present disclosure, the double-core optical fiber (4) is composed of two G652 single-mode optical fibers.

As a further improvement of the technical solutions of the present disclosure, the detection light source (6) is a wavelength-tunable narrow-linewidth laser light source.

The present disclosure has the following advantages:

(1) The fiber-optic photoacoustic sensing probe (5) is provided with the sound-insulated housing (15) with the plurality of diffusion micropores (13), which not only retains a characteristic of diffusive gas measurement of a sensor, but also makes the fiber-optic photoacoustic sensing probe (5) capable of isolating high-frequency noise.

(2) The technical solutions of the present disclosure combine a method for actively selecting a working frequency and a narrowband detection technology of a lock-in amplifier. This greatly reduces an error caused by the ambient noise when a fiber-optic photoacoustic sensor measures a gas concentration, greatly improves reliability and stability of the system without increasing a cost of the fiber-optic photoacoustic sensing system, retains advantages of the system, for example, essential safety and support for remote measurement, and provides a highly competitive technical solution for highly sensitive and reliable fiber-optic gas sensing.

Figure 1:
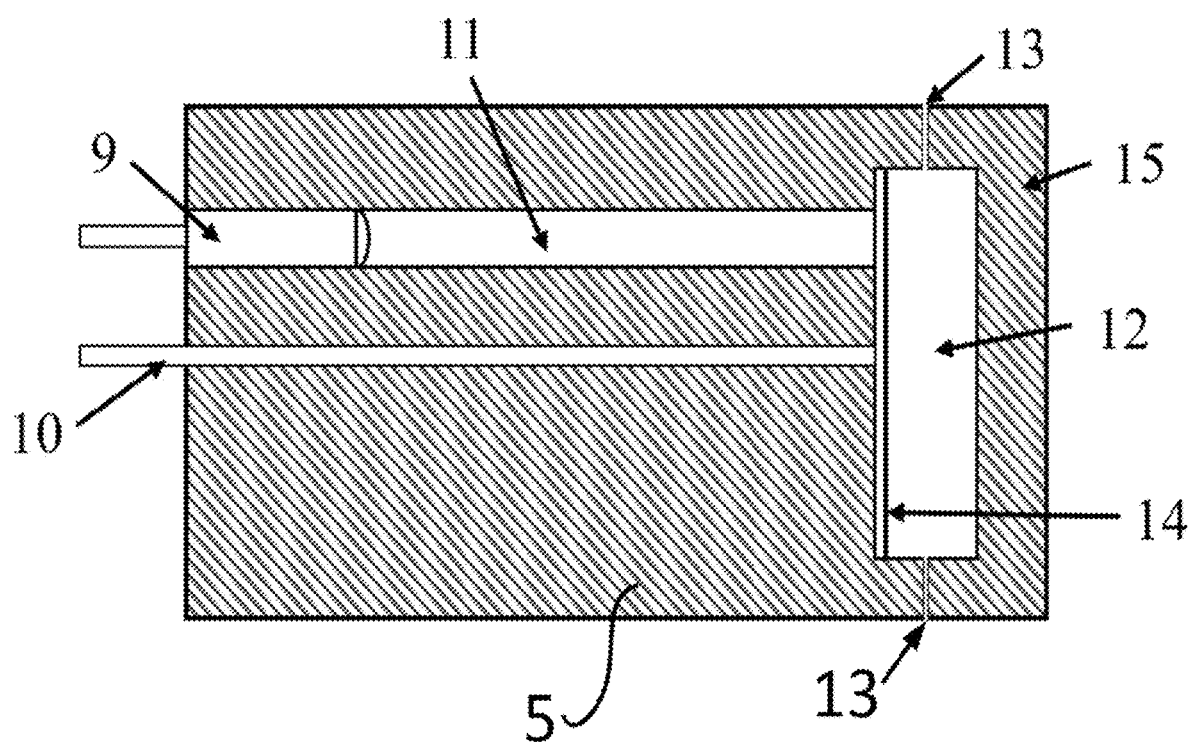
FIG. 1 is a schematic cross-sectional structural diagram of a fiber-optic photoacoustic sensing probe according to an embodiment of the present disclosure.

In the figures: signal collection and processing circuit 1; laser light source drive circuit 2; photoacoustic excitation light source 3; double-core optical fiber 4; fiber-optic photoacoustic sensing probe 5; detection light source 6; fiber-optic circulator 7; photodetector 8; fiber-optic collimator 9; single-mode optical fiber 10; photoacoustic microcavity 11; miniature air chamber 12; diffusion micropore 13; sound-sensitive diaphragm 14; sound-insulated housing 15.

DETAILED DESCRIPTION

In order to make the objectives, technical solutions, and advantages of embodiments of the present disclosure clearer, the following clearly and completely describes the technical solutions in the embodiments of the present disclosure with reference to the embodiments of the present disclosure. Apparently, the described embodiments are some rather than all of the embodiments. All other embodiments obtained by a person of ordinary skill in the art based on the embodiments of the disclosure without inventive efforts shall fall within the protection scope of the present disclosure.

The technical solutions of the present disclosure will be further described below with reference to accompanying drawings and specific embodiments in the specification.

Embodiment 1

FIG. 1 is a schematic cross-sectional structural diagram of a fiber-optic photoacoustic sensing probe 5. The fiber-optic photoacoustic sensing probe 5 includes: a fiber-optic collimator 9, a single-mode optical fiber 10, a photoacoustic microcavity 11, a miniature air chamber 12, a diffusion micropore 13, a sound-sensitive diaphragm 14, and a sound-insulated housing 15. The miniature air chamber 12 is provided inside the sound-insulated housing 15, the miniature air chamber 12 is cylindrical, and a plurality of diffusion micropores 13 communicating with the outside are provided along a diameter direction of the miniature air chamber 12. The sound-sensitive diaphragm 14 is installed inside the miniature air chamber 12. The photoacoustic microcavity 11 is deployed inside the sound-insulated housing 15 along a direction perpendicular to the miniature air chamber 12, one end of the photoacoustic microcavity 11 is connected to the outside, and the other end of the photoacoustic microcavity 11 is connected to the miniature air chamber 12. The fiber-optic collimator 9 is sealed and installed on the end, connected to the outside, of the photoacoustic microcavity 11. The single-mode optical fiber 10 is connected to the miniature air chamber 12 along a horizontal center line of the sound-insulated housing 15.

The fiber-optic collimator 9 is configured to couple laser light emitted by the photoacoustic excitation light source 3 into the photoacoustic microcavity 11. An inner diameter and a length of the photoacoustic microcavity 11 are 1 mm and 10 mm respectively. A diameter of the sound-insulated housing 15 is 20 mm, and two diffusion micropores 13 with a diameter of about 0.2 mm are provided on the sound-insulated housing 15 to accelerate diffusion of a gas into the photoacoustic microcavity 11 and isolate a high-frequency component in ambient noise. In the present disclosure, a high frequency range is 1 kHz to 20 kHz.

Figure 2:
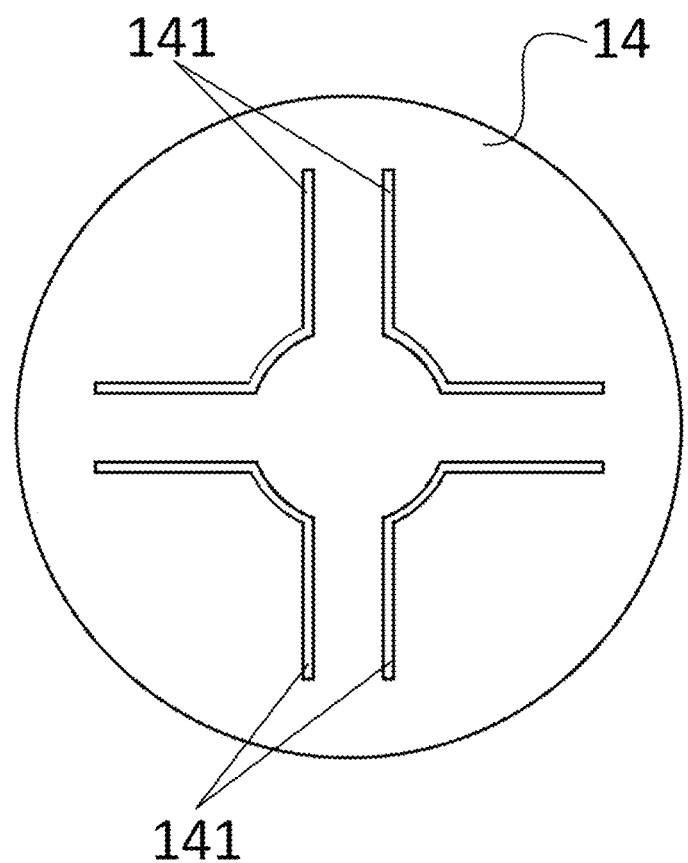
FIG. 2 is a schematic structural diagram of a sound-sensitive diaphragm according to an embodiment of the present disclosure.

FIG. 2 is a schematic structural diagram of the sound-sensitive diaphragm 14. As a high-reflectance diaphragm, the sound-sensitive diaphragm 14 includes a plurality of gaps 141 that constitute a cross-shaped beam structure at a central position of the sound-sensitive diaphragm 14. A center of the sound-sensitive diaphragm 14 and an end face of the single-mode optical fiber 10 constitute a fiber-optic Fabry-Perot interferometer. A static cavity length of the fiber-optic Fabry-Perot interferometer is about 260 μm. The to-be-measured gas diffuses into the photoacoustic microcavity 11 through the gaps 141 on the diaphragm. The sound-sensitive diaphragm 14 is fabricated by using a micro electromechanical system (MEMS) process. A diameter of the diaphragm is 10 mm and a width of the gap 141 on the diaphragm is 5 μm.

A working principle of the fiber-optic photoacoustic sensing probe 5 is as follows: The gas enters the photoacoustic microcavity 11 through the gaps 141 on the sound-sensitive diaphragm 14 after diffusing into the miniature air chamber 12 through the plurality of diffusion micropores 13. Photoacoustic excitation light is incident into the photoacoustic microcavity 11 through the fiber-optic collimator 9, and then excited to generate a photoacoustic pressure wave to cause the sound-sensitive diaphragm 14 to vibrate periodically. The end face of the single-mode optical fiber 10 and the sound-sensitive diaphragm 14 constitute the fiber-optic Fabry-Perot interferometer. The interferometer is used to measure a deflection of the diaphragm and invert a concentration of the to-be-measured gas. The plurality of diffusion micropores 13 are provided on the sound-insulated housing. These diffusion micropores 13 are equivalent to a low-pass filter when being used to isolate the ambient noise. That is, only a low-frequency component in the ambient noise can pass through these diffusion micropores 13, while the high-frequency component is "blocked" outside the photoacoustic sensing probe. A cut-off frequency of the diffusion micropore 13 is related to a quantity and sizes of diffusion micropores 13. In the present disclosure, a low frequency range is: 0 Hz to 1000 Hz. These diffusion micropores 13 not only can isolate high-frequency ambient noise, but also can accelerate diffusion of the gas into the photoacoustic microcavity and reduce response time of a system. A laser is turned off before gas measurement. At first, the ambient noise is detected, and spectrum analysis is performed on the noise. Based on a spectrum analysis result, a frequency with less ambient noise is selected as a working frequency of the system. In addition, a narrowband detection technology of a lock-in amplifier is used to greatly reduce interference caused by the ambient noise to a fiber-optic photoacoustic gas concentration detection sensor.

Figure 3:
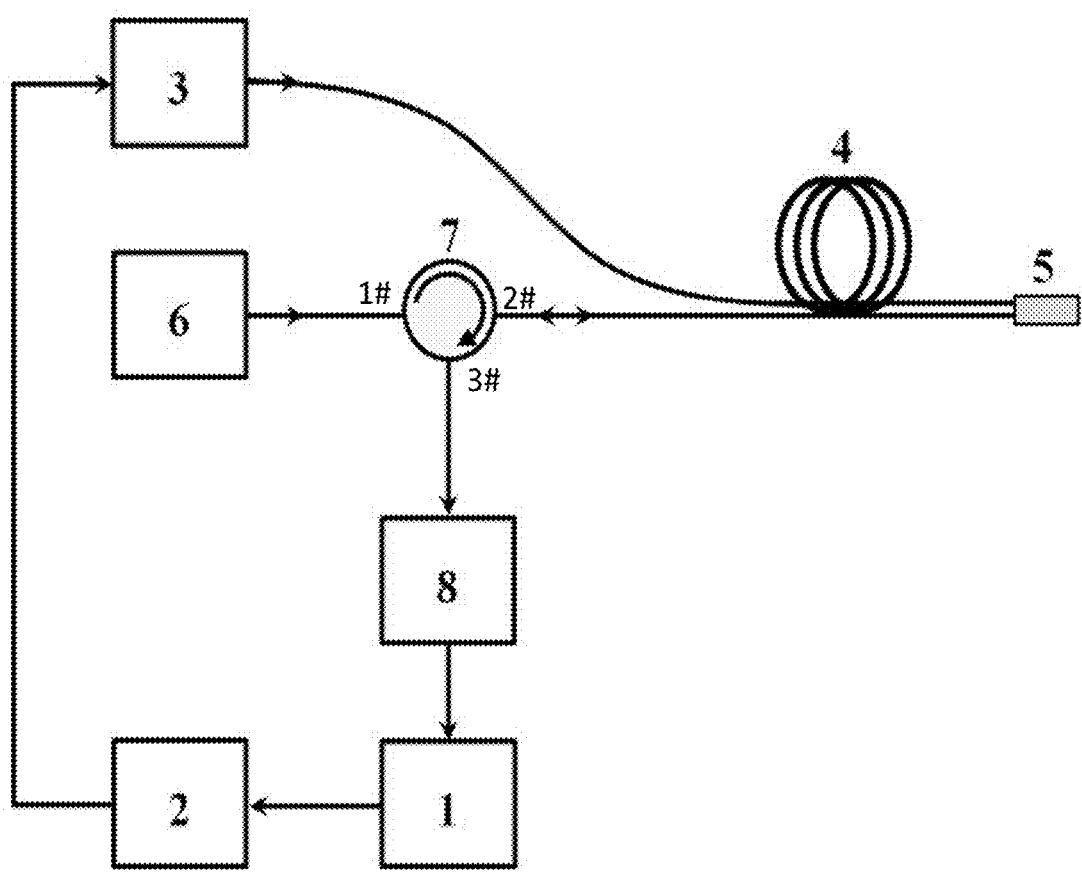
FIG. 3 is a schematic structural diagram of a system embodiment according to the present disclosure.

As shown in FIG. 3, a fiber-optic photoacoustic gas sensing system includes: a signal collection and processing circuit 1, a laser light source drive circuit 2, a photoacoustic excitation light source 3, a double-core optical fiber 4, a fiber-optic photoacoustic sensing probe 5, a detection light source 6, a fiber-optic circulator 7, and a photodetector 8. An input terminal of the photodetector 8 is connected to port 3# of the fiber-optic circulator 7, and an output terminal of the photodetector 8, the signal collection and processing circuit 1, the laser light source drive circuit 2, and the photoacoustic excitation light source 3 are connected in series and then connected to the fiber-optic photoacoustic sensing probe 5 by using one optical fiber of the double-core optical fiber 4. The detection light source 6 is connected to port 1# of the fiber-optic circulator 7, and port 2# of the fiber-optic circulator 7 is connected to the fiber-optic photoacoustic sensing probe 5 by using the other optical fiber of the double-core optical fiber 4.

The fiber-optic circulator 7 transmits, to port 2#, an optical signal input from port 1#, and transmits, to port 3#, an optical signal input from port 2#, realizing irreversibility of an optical path. The fiber-optic circulator 7 has advantages of high isolation, a low insertion loss, a low polarization dependent loss (PDL), low polarization mode dispersion, and good environmental stability.

A working principle of the system is as follows: The signal collection and processing circuit 1 controls the laser light source drive circuit 2, so that the photoacoustic excitation light source 3 is turned off. Detection light emitted by the detection light source 6 is incident into the fiber-optic photoacoustic sensing probe 5 after passing through the fiber-optic circulator 7, and returned Fabry-Perot interference signal light is received by the photodetector 8 after passing through the fiber-optic circulator 7. The signal collection and processing circuit 1 collects a photoelectric signal converted by the photodetector 8, and performs spectrum analysis on detected ambient noise through fast Fourier transform. Based on a spectrum analysis result, a low-interference frequency in the ambient noise is selected as a working frequency of subsequent photoacoustic measurement. Then, the signal collection and processing circuit 1 generates a current modulation signal to control the laser light source drive circuit 2, where the current modulation frequency is half of the selected working frequency, and the laser light source drive circuit 2 performs current and constant temperature control on the photoacoustic excitation light source 3. Laser light emitted by the photoacoustic excitation light source 3 is transmitted to the fiber-optic photoacoustic sensing probe 5 by using one optical fiber of the double-core optical fiber 4. A to-be-measured gas absorbs photoacoustic excitation light, light energy is converted into translational energy in a vibration-rotation transition process, and released heat causes periodic expansion of the gas in the fiber-optic photoacoustic sensing probe 5, so that a photoacoustic pressure wave is generated. The detection light emitted by the detection light source 6 is incident into the fiber-optic photoacoustic sensing probe 5 from the other optical fiber of the dual-core optical fiber 4 after passing through the fiber-optic circulator 7, and the returned interference signal light is received by the photodetector 8 after passing through the fiber-optic circulator 7. The signal collection and processing circuit 1 collects the photoelectric signal converted by the photodetector 8 and extracts a photoacoustic signal after digital signal processing such as filtering and second-harmonic detection-phase-locked amplification. Finally, the signal collection and processing circuit 1 calculates a concentration of the to-be-measured gas based on an amplitude of the photoacoustic signal.

A core of the signal collection and processing circuit 1 is a digital lock-in amplifier based on an FPGA, and a superposition signal of a sawtooth wave and a sine wave can be generated to perform current modulation on the photoacoustic excitation light source 3. Preferably, the core of the signal collection and processing circuit 1 is a second-harmonic detector based on a phase-locked amplification technology.

The photoacoustic excitation light source 3 is a near-infrared wavelength-tunable narrow-linewidth laser light source that can be coupled to the single-mode optical fiber, and the to-be-measured gas has a large absorption coefficient at a central wavelength of the photoacoustic excitation light source 3. Preferably, the photoacoustic excitation light source 3 is a distributed feedback (DFB) laser with a central wavelength of 1531.6 nm and a power of 15 mW. The double-core optical fiber 4 is composed of two G652 single-mode optical fibers. The detection light source 6 is a wavelength-tunable narrow-linewidth laser light source. Preferably, the detection light source 6 is a DFB laser with a central wavelength of 1550 nm and a power of 5 mW.

Figure 4:
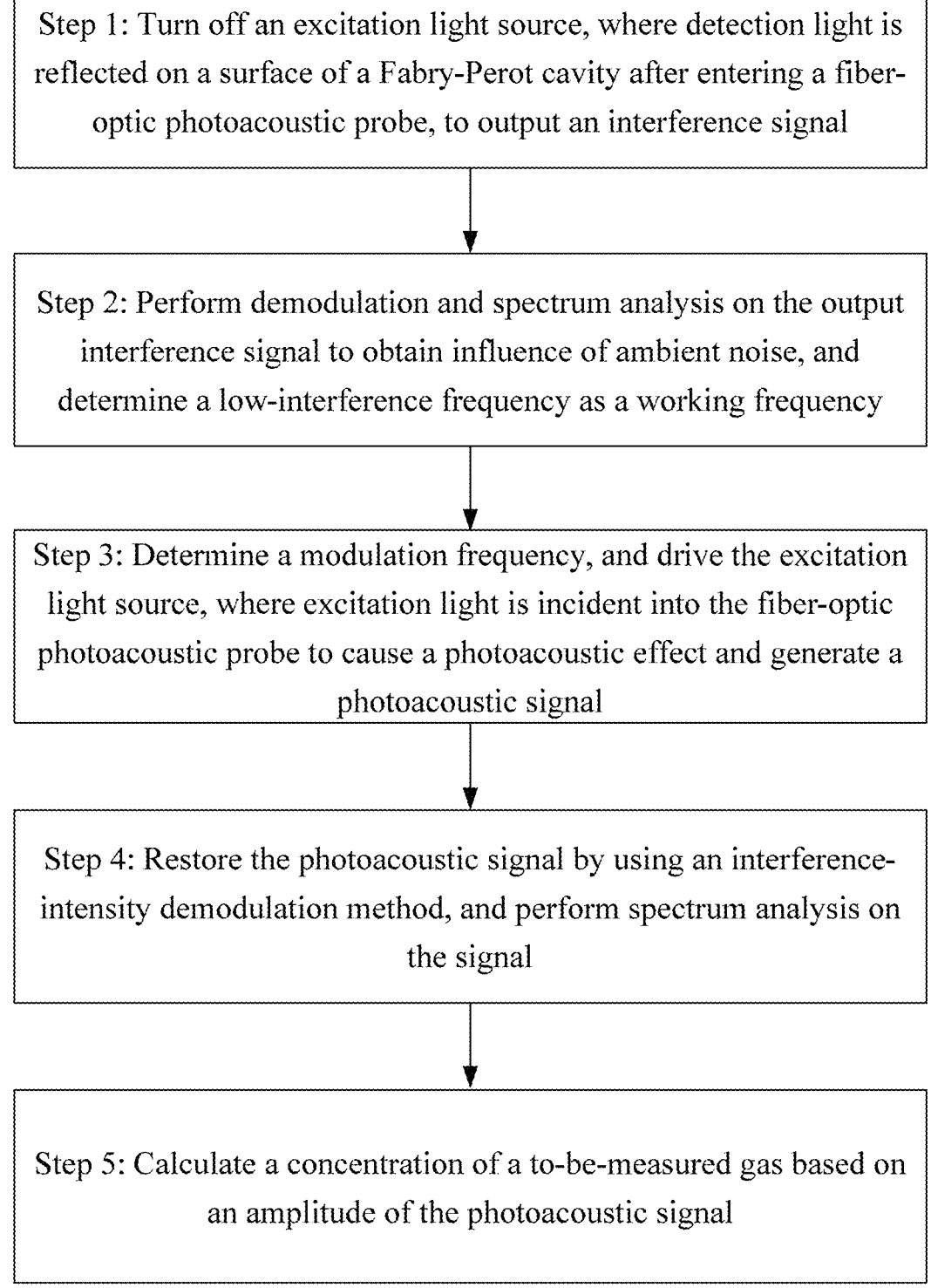
FIG. 4 is a measurement flowchart of a system embodiment according to the present disclosure.

As shown in FIG. 4, a method for actively selecting a working frequency is combined with the sound-insulated housing 15 provided with the diffusion micropores 13, high-frequency interference in the ambient noise is isolated, the sensor is enabled to work in a low frequency range, and a narrowband detection technology of a lock-in amplifier is used to greatly reduce an error caused by the ambient noise when a fiber-optic photoacoustic sensor performs gas concentration measurement. Details are as follows:

At first, the detection light emitted by the detection light source 6 is incident into the fiber-optic photoacoustic sensing probe 5 after passing through the fiber-optic circulator 7, and the returned Fabry-Perot interference signal light is received by the photodetector 8 after passing through the fiber-optic circulator 7. The signal collection and processing circuit 1 collects the photoelectric signal converted by the photodetector (8), restores the photoelectric signal by using an interference-intensity demodulation method, and performs spectrum analysis on the detected ambient noise through fast Fourier transform. Based on a frequency response of the fiber-optic photoacoustic sensing probe 5 to an external acoustic wave and the spectrum analysis result, the low-interference frequency in the ambient noise is selected within the high frequency range as the working frequency of photoacoustic measurement. After that, a measured value of an actual working frequency is compensated based on a frequency response curve of the fiber-optic photoacoustic sensing probe 5, and a compensation coefficient is a quotient of a response of the actual working frequency and a response of a default working frequency. Then, the signal collection and processing circuit 1 generates the current modulation signal to control the laser light source drive circuit 2, where the current modulation frequency is half of the selected working frequency, and the laser light source drive circuit 2 performs current and constant temperature control on the photoacoustic excitation light source 3. The laser light emitted by the photoacoustic excitation light source 3 is transmitted to the fiber-optic photoacoustic sensing probe 5 by using one optical fiber of the double-core optical fiber 4. The to-be-measured gas absorbs the photoacoustic excitation light, the light energy is converted into the translational energy in the vibration-rotation transition process, and the released heat causes periodic expansion of the gas in the fiber-optic photoacoustic sensing probe 5, so that the photoacoustic pressure wave is generated. The detection light emitted by the detection light source 6 is incident into the fiber-optic photoacoustic sensing probe 5 from the other optical fiber of the dual-core optical fiber 4 after passing through the fiber-optic circulator 7, and the returned interference signal light is received by the photodetector 8 after passing through the fiber-optic circulator 7. The signal collection and processing circuit 1 collects the photoelectric signal converted by the photodetector 8 and extracts the photoacoustic signal after digital signal processing such as filtering and second-harmonic detection-phase-locked amplification. Finally, the signal collection and processing circuit 1 calculates the concentration of the to-be-measured gas based on the amplitude of the photoacoustic signal.

Figure 6:
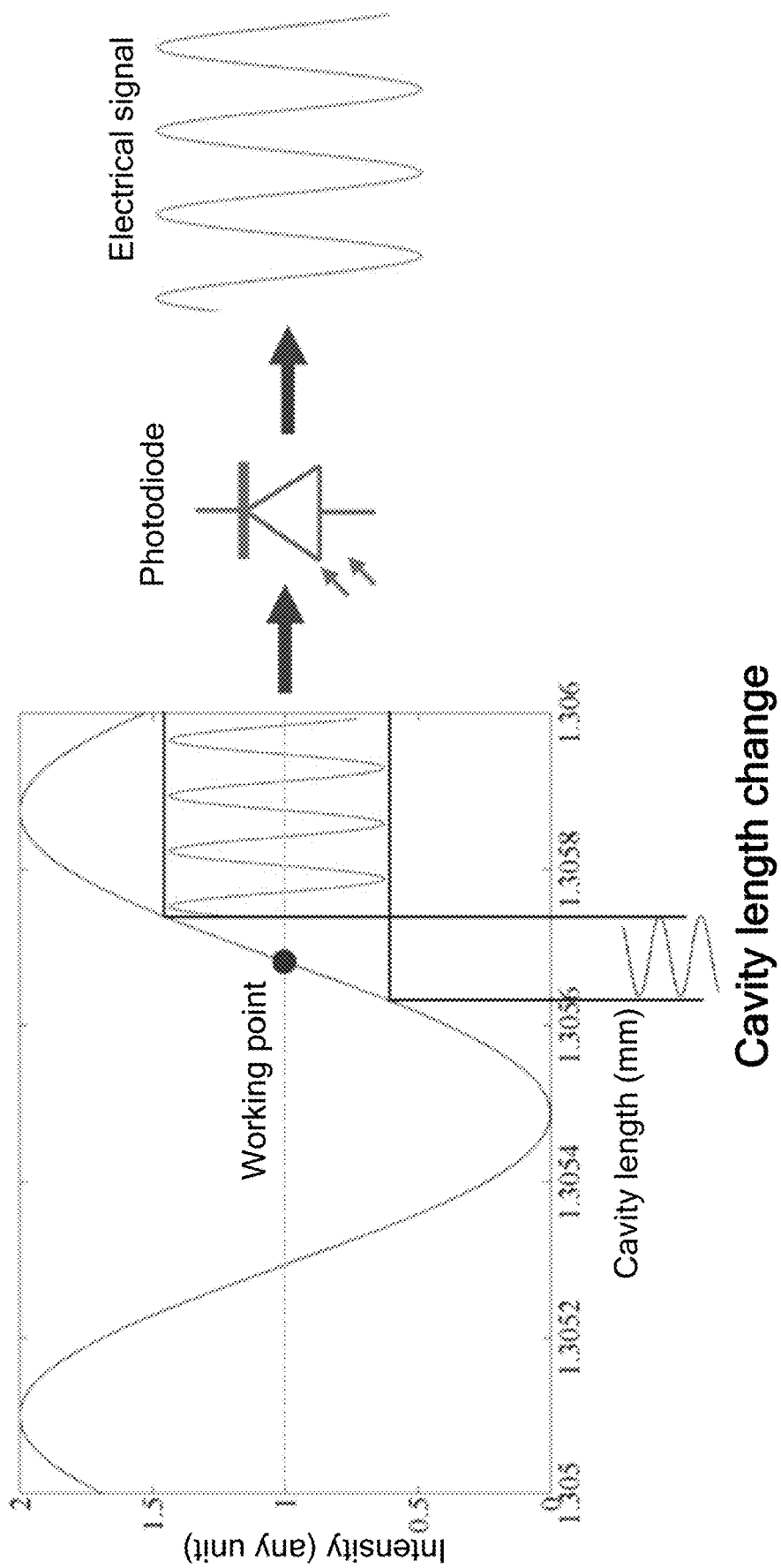
FIG. 6 is a schematic diagram of fiber-optic acoustic wave sensing based on intensity demodulation.

In the interference-intensity demodulation method, the central wavelength of the detection light source (6) is set to lock the working point at a position with a maximum absolute value of a slope of an interference curve of the fiber-optic Fabry-Perot interferometer used for photoacoustic detection (FIG. 6) in the fiber-optic photoacoustic sensing probe 5, so that acoustic wave detection has the highest sensitivity and a largest linear response range.

Figure 5:
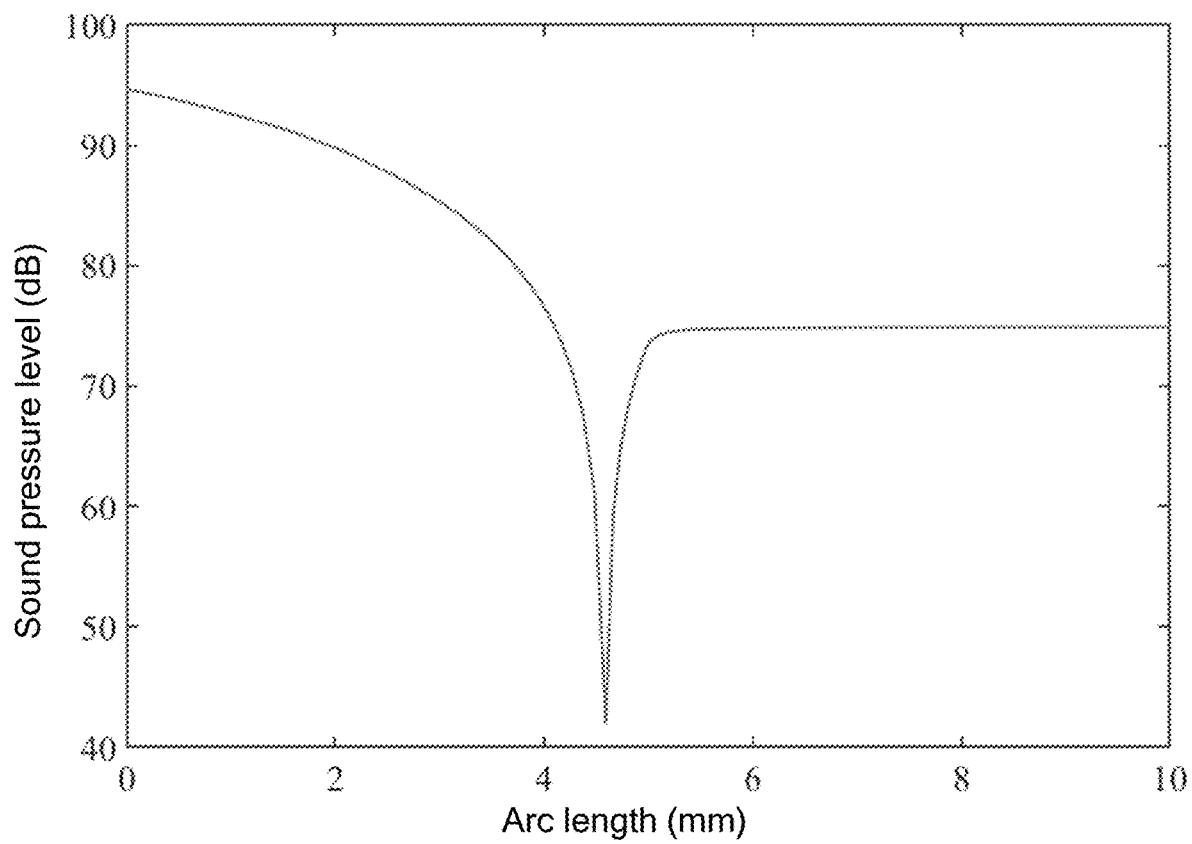
FIG. 5 shows a sound pressure change curve obtained by using acoustic simulation software when a high-frequency signal reaches a center of a diaphragm after passing through the diffusion micropore from the outside of a diffusion micropore.

FIG. 5 shows a sound pressure change curve obtained by using acoustic simulation software when a high-frequency signal reaches a center of a diaphragm after passing through the diffusion micropore from the outside of a diffusion micropore. When an acoustic wave is transmitted from the outside of a sensor to the inside of the sensor through diffusion micropores, viscous damping of the diffusion micropores to the acoustic wave blocks the acoustic wave, and sound pressure gradually declines with further penetration. When the acoustic wave passes through the micropores, the acoustic wave is reflected many times in an inner cavity, and certain superposition enhancement is caused, so that sound pressure inside a micropore on an inner-cavity side gradually increases as the acoustic wave approaches the inner cavity.

The foregoing embodiments are only used to explain the technical solutions of the present disclosure, and are not intended to limit the same. Although the present disclosure is described in detail with reference to the foregoing embodiments, those of ordinary skill in the art should understand that they can still modify the technical solutions described in the foregoing embodiments, or make equivalent substitutions on some technical features therein. These modifications or substitutions do not make the essence of the corresponding technical solutions deviate from the spirit and scope of the technical solutions of the embodiments of the present disclosure.

The invention claimed is:

1. A fiber-optic photoacoustic sensing probe capable of resisting interference from ambient noise, comprising a fiber-optic collimator (9), a single-mode optical fiber (10), a photoacoustic microcavity (11), a miniature air chamber (12), a diffusion micropore (13), a sound-sensitive diaphragm (14), and a sound-insulated housing (15), wherein the miniature air chamber (12) is provided inside the sound-insulated housing (15), the miniature air chamber (12) is cylindrical, and a plurality of diffusion micropores (13) communicating with the outside are provided along a diameter direction of the miniature air chamber (12); the sound-sensitive diaphragm (14) is installed inside the miniature air chamber (12), and comprises a plurality of gaps (141) that constitute a cross-shaped beam structure at a central position of the sound-sensitive diaphragm (14); the photoacoustic microcavity (11) is deployed inside the sound-insulated housing (15) along a direction perpendicular to the miniature air chamber (12), one end of the photoacoustic microcavity (11) is connected to the outside, and the other end of the photoacoustic microcavity (11) is connected to the miniature air chamber (12); the fiber-optic collimator (9) is sealed and installed on the end, connected to the outside, of the photoacoustic microcavity (11); the single-mode optical fiber (10) is connected to the miniature air chamber (12) along a horizontal center line of the sound-insulated housing (15); and a center of the sound-sensitive diaphragm (14) and an end face of the single-mode optical fiber (10) constitute a fiber-optic Fabry-Perot interferometer.

2. The fiber-optic photoacoustic sensing probe capable of resisting interference from ambient noise according to claim 1, wherein a working process is as follows: a gas enters the photoacoustic microcavity (11) through the gaps (141) on the sound-sensitive diaphragm (14) after diffusing into the miniature air chamber (12) through the plurality of diffusion micropores (13); photoacoustic excitation light is incident into the photoacoustic microcavity (11) through the fiber-optic collimator (9), and then excited to generate a photoacoustic pressure wave to cause the sound-sensitive diaphragm (14) to vibrate periodically; and a deflection of the diaphragm is measured by using the fiber-optic Fabry-Perot interferometer, and a concentration of the to-be-measured gas is inverted.

3. A sensing system using the fiber-optic photoacoustic sensing probe capable of resisting interference from ambient noise according to claim 2, comprising: a signal collection and processing circuit (1), a laser light source drive circuit (2), a photoacoustic excitation light source (3), a double-core optical fiber (4), a fiber-optic photoacoustic sensing probe (5), a detection light source (6), a fiber-optic circulator (7), and a photodetector (8), wherein an input terminal of the photodetector (8) is connected to port 3# of the fiber-optic circulator (7), and an output terminal of the photodetector (8), the signal collection and processing circuit (1), the laser light source drive circuit (2), and the photoacoustic excitation light source (3) are connected in series and then connected to the fiber-optic photoacoustic sensing probe (5) by using one optical fiber of the double-core optical fiber (4); the detection light source (6) is connected to port 1# of the fiber-optic circulator (7), and port 2# of the fiber-optic circulator (7) is connected to the fiber-optic photoacoustic sensing probe (5) by using the other optical fiber of the double-core optical fiber (4); and the signal collection and processing circuit (1) adopts a digital lock-in amplifier based on a field programmable gate array (FPGA).

4. The sensing system according to claim 3, wherein a working process comprises the following steps:
step 1: turning off the photoacoustic excitation light source (3), wherein the detection light is reflected on a surface of the fiber-optic Fabry-Perot interferometer after entering the fiber-optic photoacoustic sensing probe (5), to output an interference signal;
step 2: performing demodulation and spectrum analysis on the output interference signal to obtain influence of ambient noise, and then determining a low-interference frequency as a working frequency;
step 3: driving the photoacoustic excitation light source (3) after determining a modulation frequency, wherein the excitation light is incident into the fiber-optic photoacoustic sensing probe (5) to cause a photoacoustic effect and generate a photoacoustic signal;
step 4: restoring the photoacoustic signal by using an interference-intensity demodulation method, and performing spectrum analysis on the signal; and
step 5: calculating a concentration of a to-be-measured gas based on an amplitude of the photoacoustic signal.

5. The sensing system according to claim 4, wherein a method for determining the low-interference frequency as the working frequency in step 2 is as follows: the detection light emitted by the detection light source (6) is incident into the fiber-optic photoacoustic sensing probe (5) after passing through the fiber-optic circulator (7), and returned Fabry-Perot interference signal light is received by the photodetector (8) after passing through the fiber-optic circulator (7);

the signal collection and processing circuit (1) collects a photoelectric signal converted by the photodetector (8), restores an acoustic wave signal by using the interference-intensity demodulation method, and performs spectrum analysis on the detected ambient noise through fast Fourier transform; and the low-interference frequency in the ambient noise is selected, within a high frequency range and based on a frequency response of the fiber-optic photoacoustic sensing probe (5) to an external acoustic wave and a spectrum analysis result, as the working frequency of photoacoustic measurement.

6. The sensing system according to claim 4, wherein the modulation frequency in step 3 is set to half of the working frequency.

7. The sensing system according to claim 4, wherein the restoring the photoacoustic signal by using an interference-intensity demodulation method specifically comprises: setting a central wavelength of the detection light source (6) to lock a working point at a position with a maximum absolute value of a slope of an interference curve of the fiber-optic Fabry-Perot interferometer used for photoacoustic detection in the fiber-optic photoacoustic sensing probe (5), so that acoustic wave detection has the highest sensitivity and a largest linear response range.

8. The sensing system according to claim 3, wherein the photoacoustic excitation light source (3) is a near-infrared wavelength-tunable narrow-linewidth laser light source that can be coupled to the single-mode optical fiber.

9. The sensing system according to claim 3, wherein the double-core optical fiber (4) is composed of two G652 single-mode optical fibers.

10. The sensing system according to claim 3, wherein the detection light source (6) is a wavelength-tunable narrow-linewidth laser light source.

11. A sensing system using the fiber-optic photoacoustic sensing probe capable of resisting interference from ambient noise according to claim 1, comprising: a signal collection and processing circuit (1), a laser light source drive circuit (2), a photoacoustic excitation light source (3), a double-core optical fiber (4), a fiber-optic photoacoustic sensing probe (5), a detection light source (6), a fiber-optic circulator (7), and a photodetector (8), wherein an input terminal of the photodetector (8) is connected to port 3# of the fiber-optic circulator (7), and an output terminal of the photodetector (8), the signal collection and processing circuit (1), the laser light source drive circuit (2), and the photoacoustic excitation light source (3) are connected in series and then connected to the fiber-optic photoacoustic sensing probe (5) by using one optical fiber of the double-core optical fiber (4); the detection light source (6) is connected to port 1# of the fiber-optic circulator (7), and port 2# of the fiber-optic circulator (7) is connected to the fiber-optic photoacoustic sensing probe (5) by using the other optical fiber of the double-core optical fiber (4); and the signal collection and processing circuit (1) adopts a digital lock-in amplifier based on a field programmable gate array (FPGA).

12. The sensing system according to claim 11, wherein a working process comprises the following steps:
step 1: turning off the photoacoustic excitation light source (3), wherein the detection light is reflected on a surface of the fiber-optic Fabry-Perot interferometer after entering the fiber-optic photoacoustic sensing probe (5), to output an interference signal;
step 2: performing demodulation and spectrum analysis on the output interference signal to obtain influence of ambient noise, and then determining a low-interference frequency as a working frequency;
step 3: driving the photoacoustic excitation light source (3) after determining a modulation frequency, wherein the excitation light is incident into the fiber-optic photoacoustic sensing probe (5) to cause a photoacoustic effect and generate a photoacoustic signal;
step 4: restoring the photoacoustic signal by using an interference-intensity demodulation method, and performing spectrum analysis on the signal; and
step 5: calculating a concentration of a to-be-measured gas based on an amplitude of the photoacoustic signal.

13. The sensing system according to claim 12, wherein a method for determining the low-interference frequency as the working frequency in step 2 is as follows: the detection light emitted by the detection light source (6) is incident into the fiber-optic photoacoustic sensing probe (5) after passing through the fiber-optic circulator (7), and returned Fabry-Perot interference signal light is received by the photodetector (8) after passing through the fiber-optic circulator (7); the signal collection and processing circuit (1) collects a photoelectric signal converted by the photodetector (8), restores an acoustic wave signal by using the interference-intensity demodulation method, and performs spectrum analysis on the detected ambient noise through fast Fourier transform; and the low-interference frequency in the ambient noise is selected, within a high frequency range and based on a frequency response of the fiber-optic photoacoustic sensing probe (5) to an external acoustic wave and a spectrum analysis result, as the working frequency of photoacoustic measurement.

14. The sensing system according to claim 12, wherein the modulation frequency in step 3 is set to half of the working frequency.

15. The sensing system according to claim 12, wherein the restoring the photoacoustic signal by using an interference-intensity demodulation method specifically comprises: setting a central wavelength of the detection light source (6) to lock a working point at a position with a maximum absolute value of a slope of an interference curve of the fiber-optic Fabry-Perot interferometer used for photoacoustic detection in the fiber-optic photoacoustic sensing probe (5), so that acoustic wave detection has the highest sensitivity and a largest linear response range.

16. The sensing system according to claim 11, wherein the photoacoustic excitation light source (3) is a near-infrared wavelength-tunable narrow-linewidth laser light source that can be coupled to the single-mode optical fiber.

17. The sensing system according to claim 11, wherein the double-core optical fiber (4) is composed of two G652 single-mode optical fibers.

18. The sensing system according to claim 11, wherein the detection light source (6) is a wavelength-tunable narrow-linewidth laser light source.

* * * * *